US009970884B1

(12) United States Patent
Nikitin et al.

(10) Patent No.: US 9,970,884 B1
(45) Date of Patent: May 15, 2018

(54) APPARATUS AND A METHOD FOR INSPECTING A LIGHT TRANSMISSIVE OPTICAL COMPONENT

(71) Applicant: Hong Kong Applied Science and Technology Research Institute Company Limited, Shatin (HK)

(72) Inventors: Vladislav Nikitin, Ma On Shan (HK); Anna Liu, Ma On Shan (HK); Changli Wu, Shen Zhen (CN)

(73) Assignee: Hong Kong Applied Science and Technology Research Institute Company Limited, Hong Kong Science Park, Shatin (HK)

( * ) Notice: Subject to any disclaimer, the term of this patent is extended or adjusted under 35 U.S.C. 154(b) by 0 days. days.

(21) Appl. No.: 15/499,959

(22) Filed: Apr. 28, 2017

(51) Int. Cl.
*G01N 21/00* (2006.01)
*G01N 21/88* (2006.01)
*G01N 21/958* (2006.01)
*H04N 17/00* (2006.01)

(52) U.S. Cl.
CPC ....... *G01N 21/8806* (2013.01); *G01N 21/958* (2013.01); *H04N 17/002* (2013.01); *G01N 2021/8825* (2013.01); *G01N 2021/8835* (2013.01); *G01N 2021/8841* (2013.01); *G01N 2021/9583* (2013.01)

(58) Field of Classification Search
CPC ......... G01N 21/958; G01N 2021/8825; G01N 2021/8835; G01N 2021/8841; G01N 2021/9583; H04N 17/002
USPC ....................... 356/237.1–237.6, 239.1–239.8
See application file for complete search history.

(56) References Cited

U.S. PATENT DOCUMENTS 7,027,144 B2   4/2006  Morita et al.

FOREIGN PATENT DOCUMENTS

| CN | 1090042 A     | 7/1994  |
| CN | 203688465 U   | 2/2014  |
| CN | 103743761 A   | 4/2014  |
| CN | 204758502 U   | 11/2015 |
| CN | 106537110 A   | 3/2017  |

(Continued)

OTHER PUBLICATIONS

International Search Report for PCT/CN2017/083450, State Intell. Prop. Office of the P.R. China, dated Jan. 25, 2018.

*Primary Examiner* — Tri T Ton

(57) ABSTRACT

An apparatus for inspecting a light transmissive optical component comprises an image capturing module arranged on a first side of a support configured to hold a light transmissive optical component while it is being inspected. One or more first illuminating means are arranged on the first side of the support and adapted to illuminate from a first side of a light transmissive optical component held by the support. One or more second illuminating means are arranged on a second side of the support and adapted to illuminate from a second side of the light transmissive optical component held by the support, the second side of the support opposing the first side of said support. One or more third illuminating means arranged on the second side of the support and adapted to provide transmissive illumination at the second side of the light transmissive optical component held by the support, the third illuminating means comprises one or more of an illuminating surface and a light blocking surface selectively operable and are arranged to face and substantially align with the second illuminating means on the second side of the support.

20 Claims, 11 Drawing Sheets

(56) References Cited

FOREIGN PATENT DOCUMENTS

| | | |
|---|---|---|
| JP | H095248 | 1/1997 |
| JP | 2009288121 | 5/2008 |
| KR | 20150099956 | 9/2015 |
| WO | 123870 | 4/2001 |

APPARATUS AND A METHOD FOR INSPECTING A LIGHT TRANSMISSIVE OPTICAL COMPONENT

FIELD OF THE INVENTION

The invention relates to the field of inspecting light transmissive optical components. Particularly but not exclusively, the invention relates to an apparatus and a method for inspecting defects in light transmissive optical components such as optical lenses.

BACKGROUND OF THE INVENTION

Optical instruments such as cameras and/or video cameras have been so commonly used in daily life that variations of them have been widely incorporated in portable electronic devices such as smart phones, tablet computers, as well as mobile surveillance units such as digital image and/or video recorders for home use or installable in vehicles or in buildings. Very often, these optical instruments or their variations comprise one or more light transmissive optical components such as optical lenses, and during their manufacturing process, inspection of these optical lenses for defects has always been challenging. Lens inspection generally requires specialized skills of the inspector, and the process can be highly time and labor intensive. Existing methods may involve manual and visual checking for defects at the lens such as black spots, scratches, dust or dirt particles, air bubbles, flow marks and/or other injection or coating defects. Quality of such inspections is thus largely dependent on judgement of the inspecting individual, which could be subjective and inconsistent. Accuracy of the inspections may further be compromised, especially during a mass production process where a large number of lenses are to be manually and visually inspected. It would be understandable that continuous and repetitive visual checking for long hours may cause vision fatigue or even damage to one's eyesight, which may further deteriorate quality and reliability of the inspection.

OBJECTS OF THE INVENTION

An object of the present invention is to provide an apparatus for inspecting a light transmissive optical component such as an optical lens.

Another object of the present invention is to mitigate or obviate to some degree one or more problems associated with known means for inspecting light transmissive optical components, or at least to provide a useful alternative.

The above objects are met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

In a first main aspect, the invention provides an apparatus for inspecting a light transmissive optical component, comprising an image capturing module arranged on a first side of a support configured to hold a light transmissive optical component whilst it is being inspected; one or more first illuminating means arranged on the first side of the support and adapted to illuminate from a first side of a light transmissive optical component held by said support; one or more second illuminating means arranged on a second side of the support and adapted to illuminate from a second side of the light transmissive optical component held by said support, the second side of the support opposing the first side of said support; wherein the one or more first illuminating means and the one or more second illuminating means are adapted to be selectively switched on to enable the image capturing module to capture one or more bright field images and dark field images of the light transmissive optical component held by the support.

In a second main aspect, the invention provides a system for inspecting a light transmissive optical component comprising two or more apparatuses of the first aspect.

In a third main aspect, the invention provides a method of conducting an automated inspection of light transmissive optical components using the apparatus of the first aspect. The method comprises positioning a light transmissive optical component at an image capturing position of the apparatus; actuating one or more of the first illuminating means and the second illuminating means of the apparatus; capturing a sequence of images of the light transmissive optical component under different configurations of the first illuminating means and the second illuminating means; and analyzing the sequence of images to identify a defect of the light transmissive optical component being inspected.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figure, of which:

FIG. 3 shows the apparatus of FIG. 1 with the second illuminating means being selectively switched on;

FIG. 6 shows the apparatus of FIG. 1 with the second illuminating means and, optionally, the third illuminating means being selectively switched on;

FIG. 8 shows the apparatus of FIG. 1 with any one or more of the first illuminating means, the second illuminating means and the third illuminating means being selectively switched on;

FIG. 9A shows the image captured by the apparatus of FIG. 8 with only the second illuminating means being switched on;

FIG. 9B shows the image captured by the apparatus of FIG. 8 with only the first illuminating means being switched on;

FIG. 9C shows the image captured by the apparatus of FIG. 8 with only the third illuminating means being switched on;

DESCRIPTION OF PREFERRED EMBODIMENTS

The following description is of preferred embodiments by way of example only and without limitation to the combination of features necessary for carrying the invention into effect.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Figure 1:
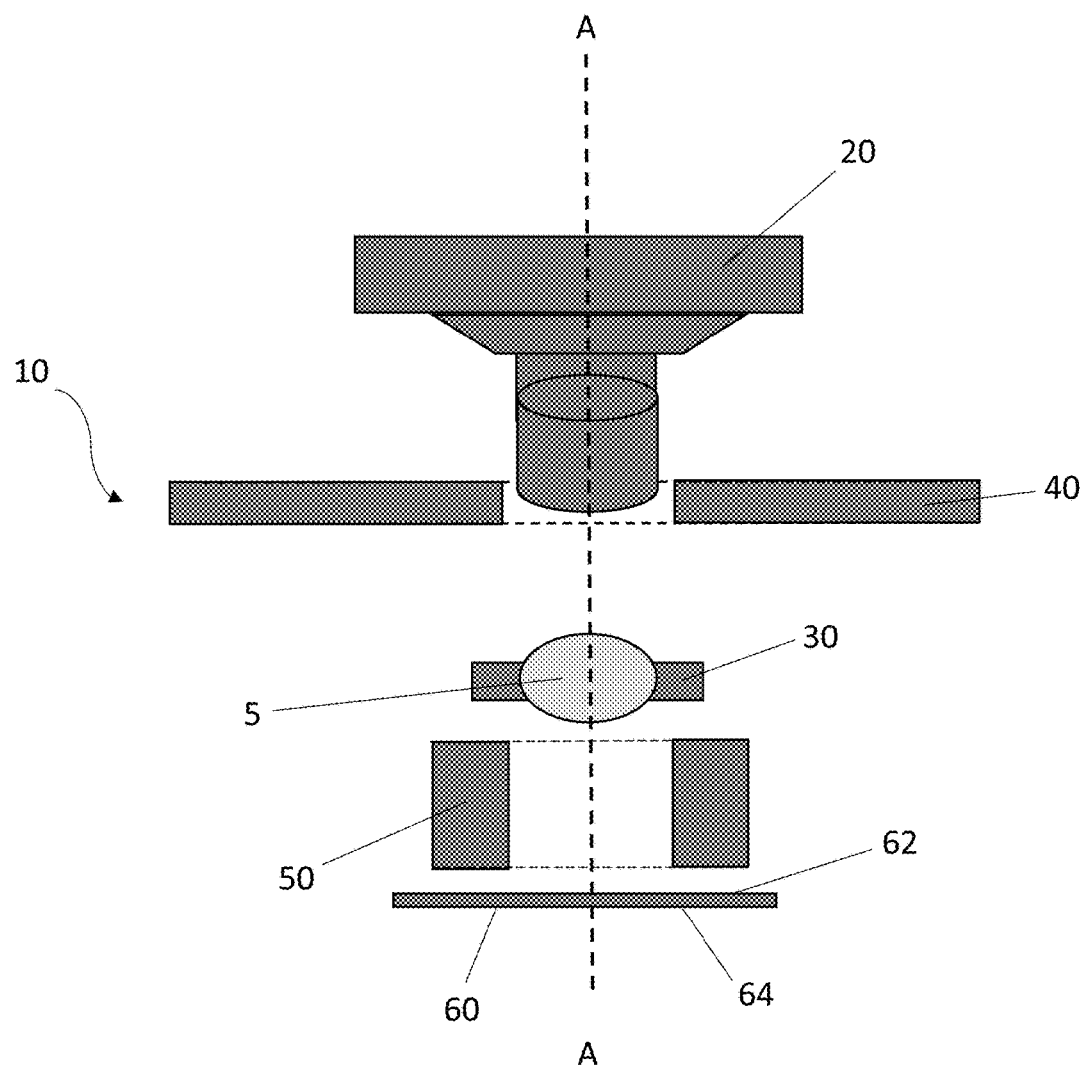
FIG. 1 is a schematic diagram showing a first embodiment of the apparatus for inspecting a light transmissive optical component according to the present invention.

Referring to FIG. 1, shown is a schematic diagram showing a first embodiment of the apparatus 10 for inspecting a light transmissive optical component 5 according to the present invention. The optical component 5 can be any light transmissive object for various purposes such as, but not limited to, optical lenses for use in cameras, camera phones, video recorders, monoculars or binoculars, telescopes, or microscopes. The optical lenses may also be formed of any suitable materials which allow light transmission such as but not limited to crystals, glasses or plastics, etc.

The apparatus 10 may comprise an observing position or means or, more specifically, an image capturing module 20 which can be one or more of a camera and a video camera adapted to capture one or more images or videos of the optical component 5 being inspected. Preferably, the image capture module 20 is adapted to be connected with one or more of a computer storage medium, image processing means and network database for outputting, transferring, storing and/or processing of the captured images and videos.

The image capturing module 20 can be arranged on a first side, such as an upper side as shown in the figure, of a support 30 which is configured to hold the optical component 5 whilst it is being inspected. In this embodiment, the apparatus 10 further comprises one or more first illuminating means 40 arranged on the first side of the support 30, and adapted to illuminate from a first side, such as an upper side as in this embodiment, of the optical component 5 held by said support 30.

The apparatus 10 may further comprise one or more second illuminating means 50 arranged on a second side, such as a lower side as shown in the figure, of the support 30, with the second side being opposite to the first side of the support 30. The second illumining means 50 is adapted to illuminate from a second side, such as a lower side as in this embodiment, of the optical component 5. Specifically, the first illuminating means 40 and the second illuminating means 50 are adapted to be selectively switched on to enable the image capturing module 20 to capture one or more bright field images and dark field images of the optical component 5 being inspected.

In one embodiment, the support 30 is movable along at least one of an x-, y- and z-coordinate axis between the first illuminating means 40 and the second illuminating means 50 to thereby align and position the supported optical component 5 in a suitable image capturing position or inspecting position. Particularly, the support 30 may further be adapted to support more than one light transmissive optical component in, for example a linear or a circular arrangement, and the support 30 may be movable or rotatable to align and position a respective one of the plurality of the optical components between the first illuminating means 40 and the second illuminating means 50.

The first illuminating means 40 may comprise an annular configuration, such as in the form of a disc-shaped illuminator arranged at the side of the image capturing module 20. The disc-shaped configuration may comprise a free space central hole substantially aligned with an axis A-A' passing through the first side and the second side of the support 30, with the axis preferably aligned also with a visible light-conveying light path towards the image capturing module 20, as shown in FIG. 1. This allows any image capturing of the optical component 5 by the image capturing module 20 to be free from being blocked or interfered with by the first illuminating means 40.

The second illuminating means 50 may also comprise an annular configuration, but in the form of, for example, a hollow cylindrical shape as shown in FIG. 1. Preferably, the cylindrical illuminator may comprise a free space central passage extending along its length, such that illumination can be provided at the peripheral side of the cylindrical wall, but with a dark background at the center for dark-field imaging. The hollow center is again preferably substantially aligned with the axis A-A' as well as the visible light-conveying light path towards the image capturing module 20.

The first and the second illuminating means 40, 50 may comprise any common visible light emitting sources such as incandescent light, fluorescent light, discharged lamp, gas discharged lamp, lasers, or light-emitting diodes (LED), etc., and each light emitting source may optionally be equipped with one or more diffusers for an uniform illumination.

In one embodiment, the apparatus 10 may further comprise a third illuminating means 60 arranged on the second, lower side of the support 30 and adapted to provide transmissive illumination to the optical component 5, as shown in the figure. The third illuminating means 60 may comprise a planar, flat or curved structure, but preferably comprises a planar structure as shown in FIG. 1, with at least one illuminating surface 64 arranged to face and substantially align with the second illuminating means 50 at the second, lower side of the support 30. Preferably, the third illuminating means 60 may comprise a light blocking surface 62 at a side distal to the image capturing module 20 and opposing the illuminating surface 64. The light blocking surface 62 is beneficial in preventing external light from interfering with the image capturing by the image capturing module 20.

Preferably, the third illuminating means 60 may comprise an electronic display unit, such as but not limited to, a liquid crystal display (LCD) or an active-matrix organic light-emitting diode (AMOLED) display, although a person skilled in the art would appreciate that any other light emitting surfaces of different shapes and configurations may also be applicable. In one embodiment, the third illuminating means 60 may comprise a LCD or a AMOLED device adapted to display one or more uniform light pattern such as a striped or circled pattern, and preferably, a uniform white-colored pattern to detect amplitude defects. The third illuminating means 60 may further comprise a mechanical shutter with dark, matte-colored blinds facing the second illuminating means 50 to mechanically block off any parasitic illumination from the illuminating surface 64 of the third illuminating means 60 when the other illuminating means 40 and/or 50 are switched on. Optionally, a retardation plate can be provided between the second and the third illuminating means 50, 60 for converting any polarized light beam from the third illuminating means 50 into light with different polarization characteristics such as circularly polarized light.

Figure 2:
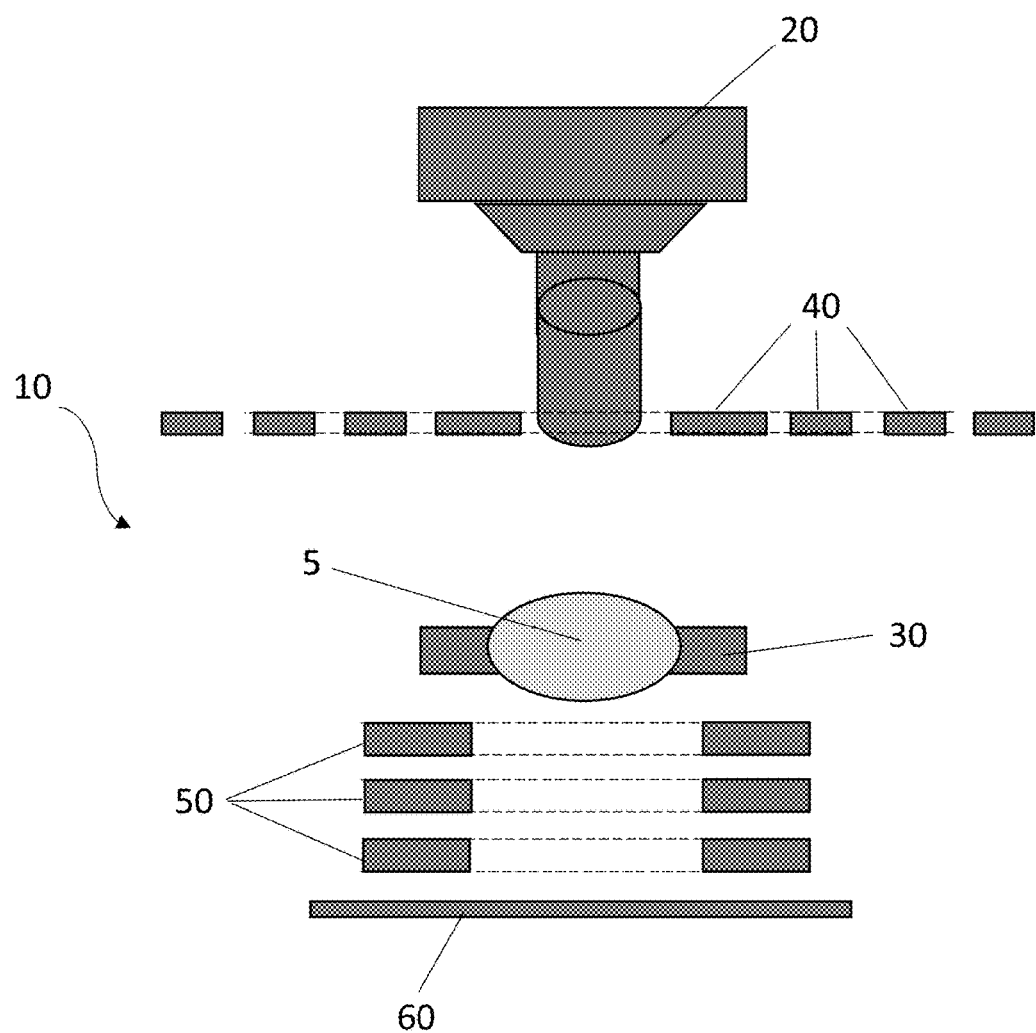
FIG. 2 is a schematic diagram showing a second embodiment of the apparatus for inspecting a light transmissive optical component according to the present invention.

Referring to FIG. 2, shown is a second embodiment of the apparatus 10 in accordance with the present invention. In this embodiment, the first illuminating means 40 comprises a plurality of first illuminating units 40, each of which is adapted to independently illuminate the optical component 5 from the first, upper side at different and/or adjustable illuminating angles. For example, the disc-shaped first illuminating means 40 may comprise a plurality of annular first illuminating units 40 arranged concentrically to one another. The plurality of annular first illuminating units 40 can be of a planar or substantially planar arrangement, although variations in positions between the illuminating units 40 may also be possible, as long as they are capable of emitting light at different angles towards the optical component 5 being inspected.

Similarly, the cylindrical second illuminating means 50 may comprise a plurality of annular second illuminating units 50, as shown in FIG. 2, each of which is adapted to independently illuminate the optical component 5 from the second, lower side at different and/or adjustable illuminating angles. For example, the plurality of annular, second illuminating units 50 can be arranged coaxially to one another to form the hollow cylinder of the second illuminating means 50, as shown in the figure.

In one further embodiment, one or more of the plurality of first illuminating units 40 and/or one or more of the plurality of second illuminating units 50 can be selectively and independently switched on to provide illumination to the optical component 5 at various and/or changing illuminating angles and/or light intensities to thereby allow variation or customization in brightness and/or contrast to the captured images.

Figure 3:
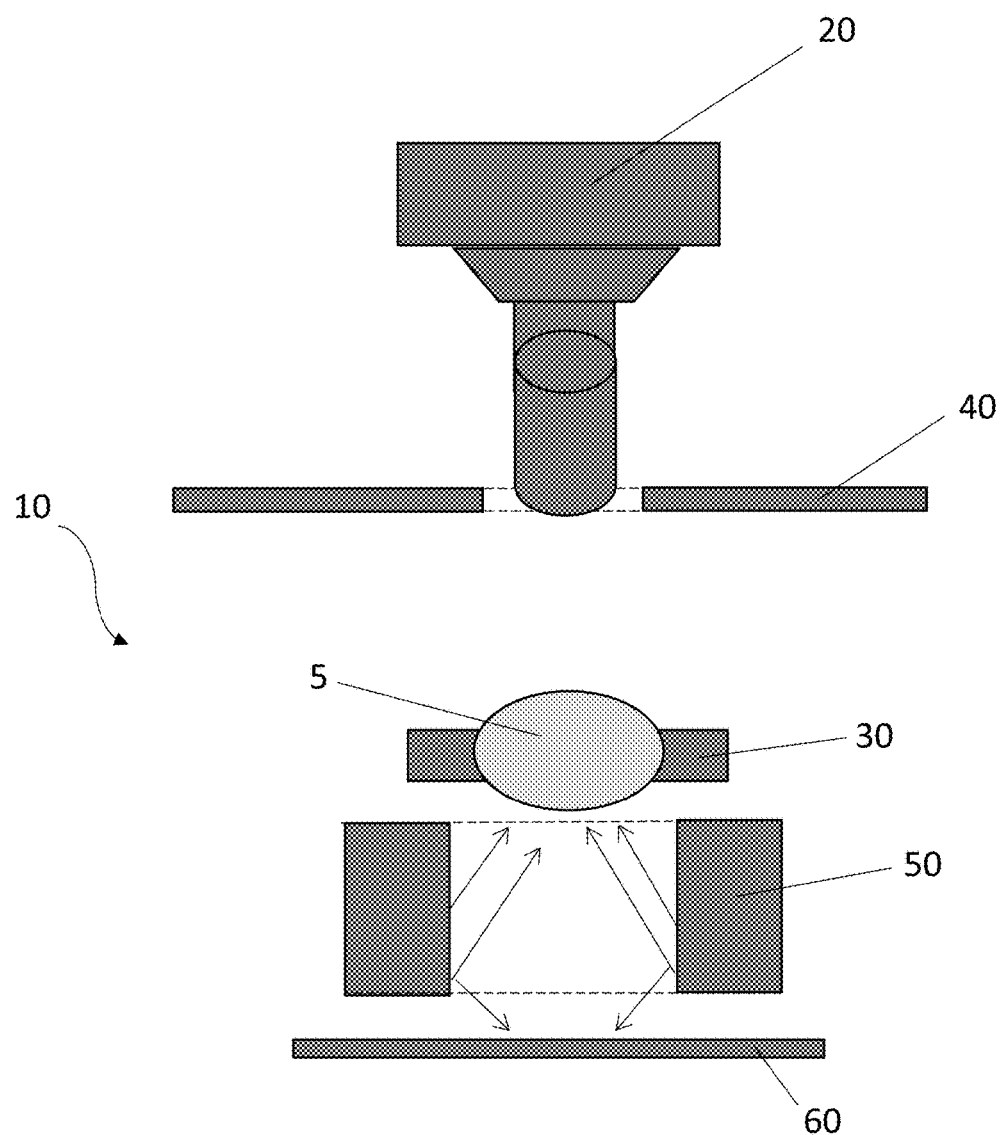

For example, FIG. 3 illustrates an embodiment of the present invention with the apparatus 10 being configured to have only the second illuminating means 50 being switched on for illumination, i.e. no light emission from the first and the third illuminating means 40, 60 to thereby allow a backside, dark-field imaging of the optical component 5. In this embodiment, a black matte surface is provided at the third illuminating means 60, such as the light blocking surface 62, to allow absorption of parasitic light from the second illuminating means 50. After positioning of the optical component 5 at an appropriate image capturing position, the image capturing module or camera unit 20 will be triggered to capture at least one image, but preferably a sequence of dark-field images of the optical component 5 at different exposure times or shutter speeds of the camera 20.

Figure 4:
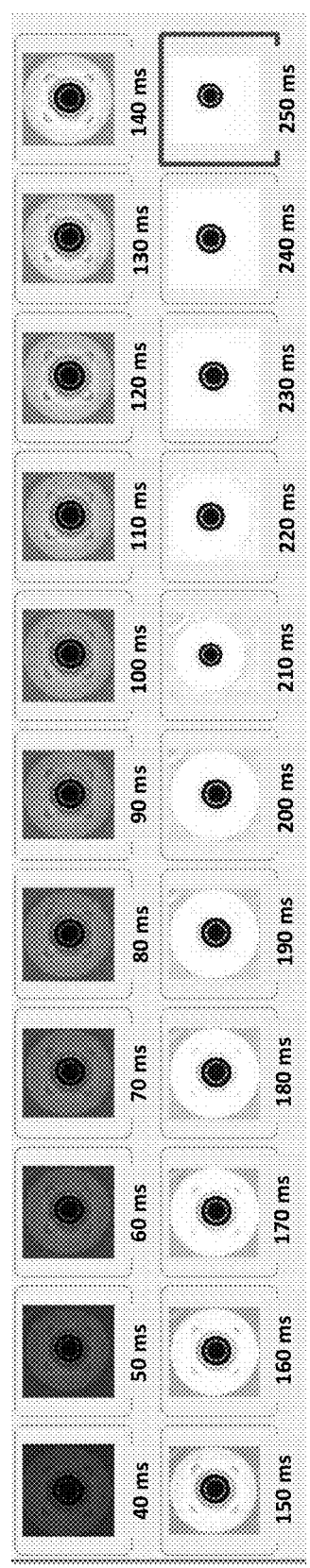
FIG. 4 shows a sequence of images captured by the apparatus of FIG. 3.
Figure 5:
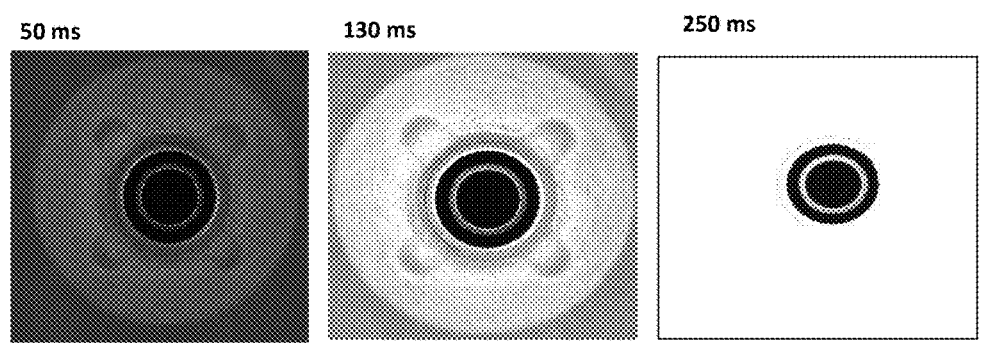
FIG. 5 shows the images captured at 50 ms, 130 ms and 250 ms by the apparatus of FIG. 3.

The sequence of dark-field images captured by the apparatus 10 of FIG. 3 so configured are shown in FIG. 4. Specifically, FIG. 4 shows the dark-field images taken at exposure times ranging from 40 ms to 250 ms, with a 10 ms interval. FIG. 5 further shows the captured dark-field images at 50 ms, 130 ms and 250 ms. It can be seen that, at a certain exposure for one region with defects to become visible, other regions of the same optical lens could be totally underexposed or overexposed. This explains why a sequence of changing exposures and, optionally, with other light settings may be required to provide a full coverage of all or most defects or defect types present at different locations of an optical lens sample, i.e. an optical component being inspected.

Accordingly, in order to allow defects of different types, which might be located at different regions of an optical component, to be clearly observable, a sequence of images captured at various configurations of the apparatus are preferably taken. The different configurations may include, but are not limited to, a changing shutter speeds of the camera and thus a varying exposure times under the illumination of one or more of the illuminating means 30, 40 and 50, and/or different configurations of the respective illumining means 30, 40 and 50, to thereby enable inspection of the optical component under one or more dark-field and bright-field illuminations. The option to inspect under dark-field and/or bright-field conditions at various illumination settings is particularly beneficial to allow defects of various types and sizes, as well as defects at different regions of the lens, be revealed at suitable contrasts and brightnesses.

Figure 6:
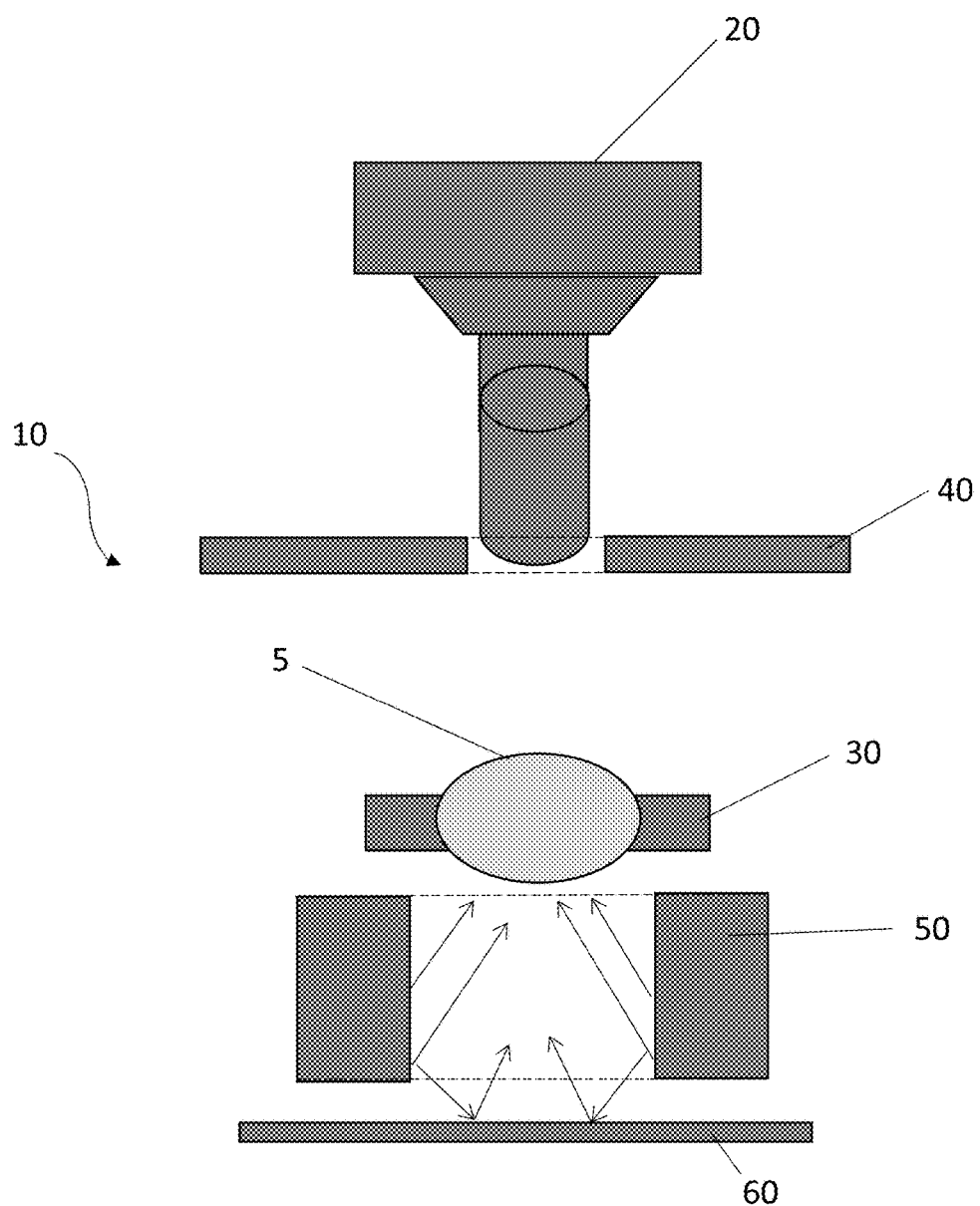
Figures 7A, 7B:
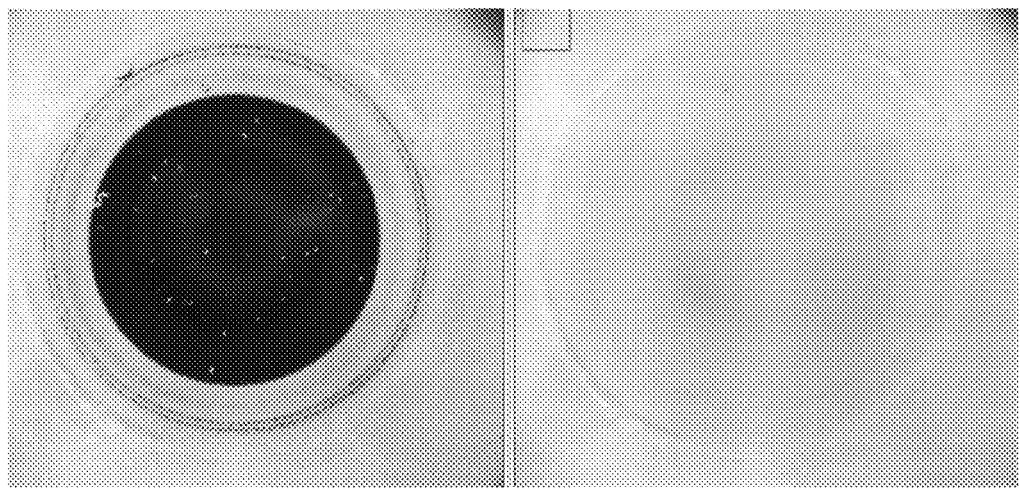
FIG. 7A shows the image captured by the apparatus of FIG. 6 with the third illuminating means being switched off and being provided with a dark matte background.
FIG. 7B shows the image captured by the apparatus of FIG. 6 with the third illuminating means being switched on without the dark matte background.

FIG. 6 illustrates another example in which the apparatus 10 is configured to have both the second illuminating means 50 and the third illuminating means 60 operable. Particularly, the third illuminating means 60, which can be a planar, back straight diffused light illuminating means such as a LCD or AMOLED device, can be switched on or off while the second illuminating means 50 is maintained on to thereby provide a change of light setting for the imaging capturing by the camera 20. The respective images captured are shown in FIGS. 7A and 7B. For example, FIG. 7A shows a dark-field image of the component 5 taken when only the second illuminating mean 50 is on, i.e. a dark-field image with black, matte background, and the image reveals a number of defects of the component 5 at high contrast. The same defects are not visible in FIG. 7B, which is a corresponding image taken when both the second and the third illuminating mean 50, 60 are switched on, i.e. an image with white matte background, with the image being overly illuminated.

Figure 8:
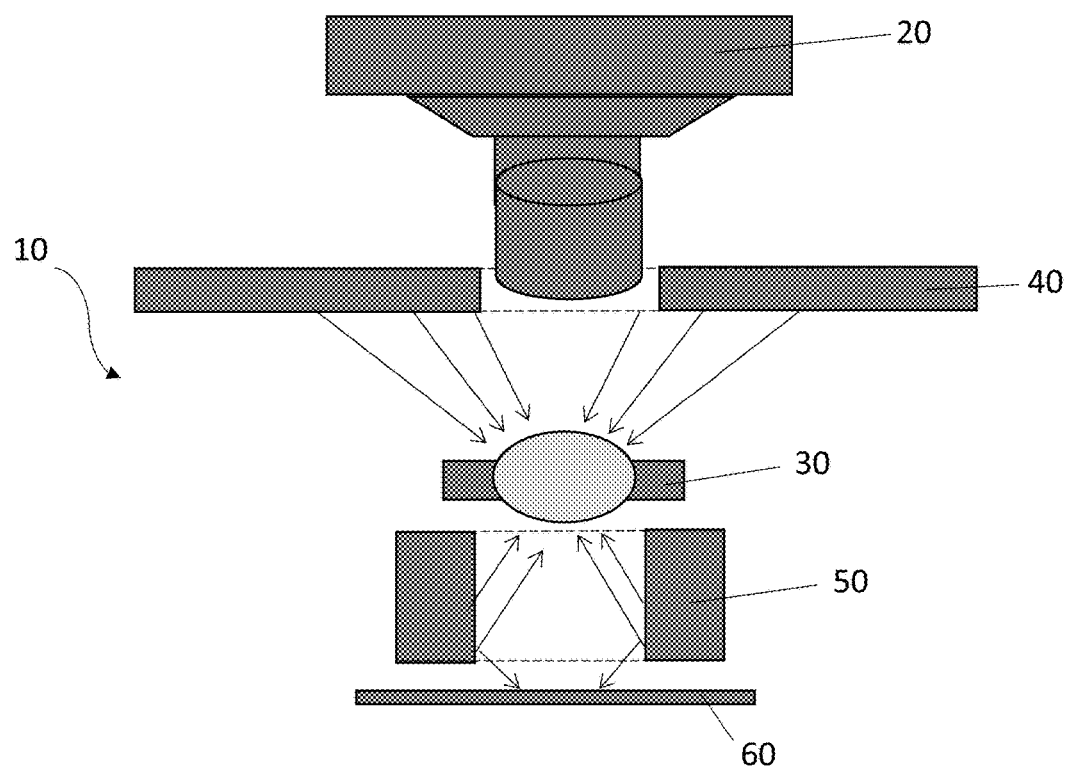
Figure 9A:
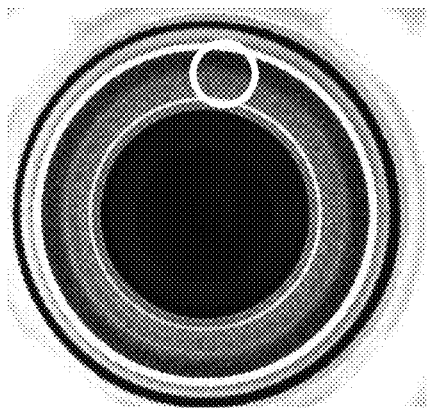
Figure 9B:
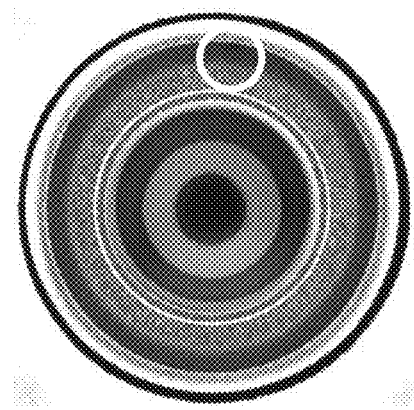
Figure 9C:
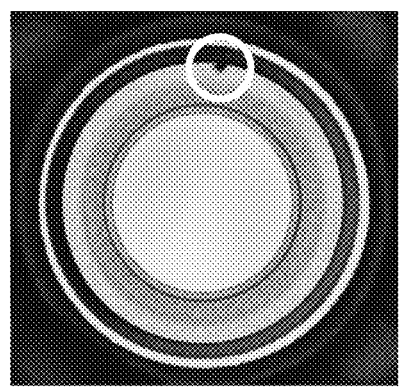

FIG. 8 illustrates a further example in which the apparatus 10 is configured to have all three of first, second, and third illuminating means 40, 50 and 60 operable. Particularly, the first illuminating means 40 is adapted to provide a front side illumination for a bright-field vision to the component 5, alternatively or additionally to the second and/or third illuminating means 50, 60. The images captured under the respective settings are shown in FIGS. 9A, 9B and 9C, with a reference target region circled in the images for comparison. Specifically, FIG. 9A shows a dark-field image of the component 5 when only the second illuminating mean 50 is switched on with little or no defect at the circled region being observable. FIG. 9B shows a front side illuminated, bright-field image of the component 5 when only the first illuminating mean 50 is switched on, and again, with little or no defect at the circled region being observable. FIG. 9C further shows a backside illuminated image of the component 5 with only the third illuminating means 60 is switched on, whereby the image reveals a clear defect, i.e. the black spot, at the circled region at high contrast.

The apparatus of the present invention may further be applied in conducting an automated inspection of one or more light transmissive optical components. For example, after an automatic positioning of a light transmissive optical component, such as an optical lens, by adjusting at least one of the x, y or z-coordinate axes of the support 30 to an appropriate image capturing position of the apparatus 10, one or more of the first, second and the third illuminating means 40, 50 and 60 can be actuated sequentially, simultaneously in any combination, or selectively to provide different or varying illuminations to the optical lens for image capturing purposes. The images can thus be captured under different fields of illumination such as bright-field, dark-field or a combination of bright and dark fields to thereby reveal defects of different types at different locations of the optical lens 5 at different contrasts. At each specific illumination setting, one or a sequence of images can be taken at changing camera shutter speeds to allow images of different exposures to be acquired for further inspection and analysis. The captured images may optionally be output, transferred, saved as digital data in one or more computer storage mediums and one or more databases, or be processed at any computer processing means prior to or after the inspection. The inspection may then either be conducted manually by a skilled operative for a semi-automated process, or automatically by one or more processors executing suitable computer software for a fully automated inspection process.

Preferably, the first, second, and third illuminating means 40, 50 and 60 may provide further variations in the illumination settings by, for example, the first illuminating means 40 comprising more than one first illuminating units 40, and/or for the second illuminating means 50 to comprise more than one second illuminating units 50, with one or more of these respective units being adapted to be selectively and independently switched on to provide adjustment on the illuminating angles and/or brightnesses.

In one preferred embodiment, prior to the inspection of a plurality of optical lens by the apparatus 10, a trial run or a so-called "self-training" process is first conducted with an aim to determine one or more preferred settings or configurations of the apparatus 10 for the inspection of, for example, a number of optical lenses with one specific structure or lens type. A process for the trial run is illustrated in the flow chart of FIG. 10 by way of example. After loading of an optical lens 5 at the support 30 (Step Ai), the lens 5 is first positioned by adjusting one or more of the x, y and/or z-coordinate axes of the support 30 to an appropriate image capturing position (Step Aii). The step is followed by actuating, one at a time, the first illuminating means 40, the second illuminating means 50, and the third illuminating means 60 in an arbitrary or a predetermined sequence. For example, the first illuminating means 40 can be first switched on while the other two illuminating means 50, 60 stay off (Step Bi). The first test image under the illumination by the first illuminating means 40 will be captured (Step Bii). Repositioning of the support 30 may optionally be required (Step C) to correct the coordinate position.

A sequence of images can be taken at changing exposure times (Step Biii), and the images showing the most suitable fields of observation will be selected and saved (Step Ei), and optionally, output to an inspection computer database (Step Eii). The first illuminating means 40 will then be switched off (Step Biv), and the next illuminating means, such as the second illuminating means 50, will be subsequently switched on and the illuminating and capturing process repeated (Step F) until all the illuminating means have been actuated in sequence.

Preferably, each of the illuminating means 40, 50, 60 may also be actuated at one or more of its preferred lighting configurations or settings, for example, if the illuminating means comprises more than one illuminating unit, or any specific combinations of such units. After each actuation of the respective illuminating means at the preferred lighting configurations, a sequence of images of the optical component 5 will be captured by the camera 20 at changing exposure times. The captured images are then analyzed and selected for further inspection.

Alternatively, the best suitable or preferred settings of the apparatus 10 can also be determined by, for example, simultaneously actuating a first combination of two illuminating means selected from the first, second and third illuminating means 40, 50, 60; and after actuation of the first combination of illuminating means, capturing a sequence of images of the optical component under different configurations of the first combination; and subsequently, simultaneously actuating a second combination of two illuminating means selected from the first, second and third illuminating means 40, 50, 60, with the second combination being different to the first combination. After actuation of the second combination of the illuminating means, a sequence of images of the optical component will also be captured under different configurations of the second combination of the illuminating means. The combined illuminating settings may provide further variations to the possible field of observations for different types of optical components and their defects.

Figure 10:
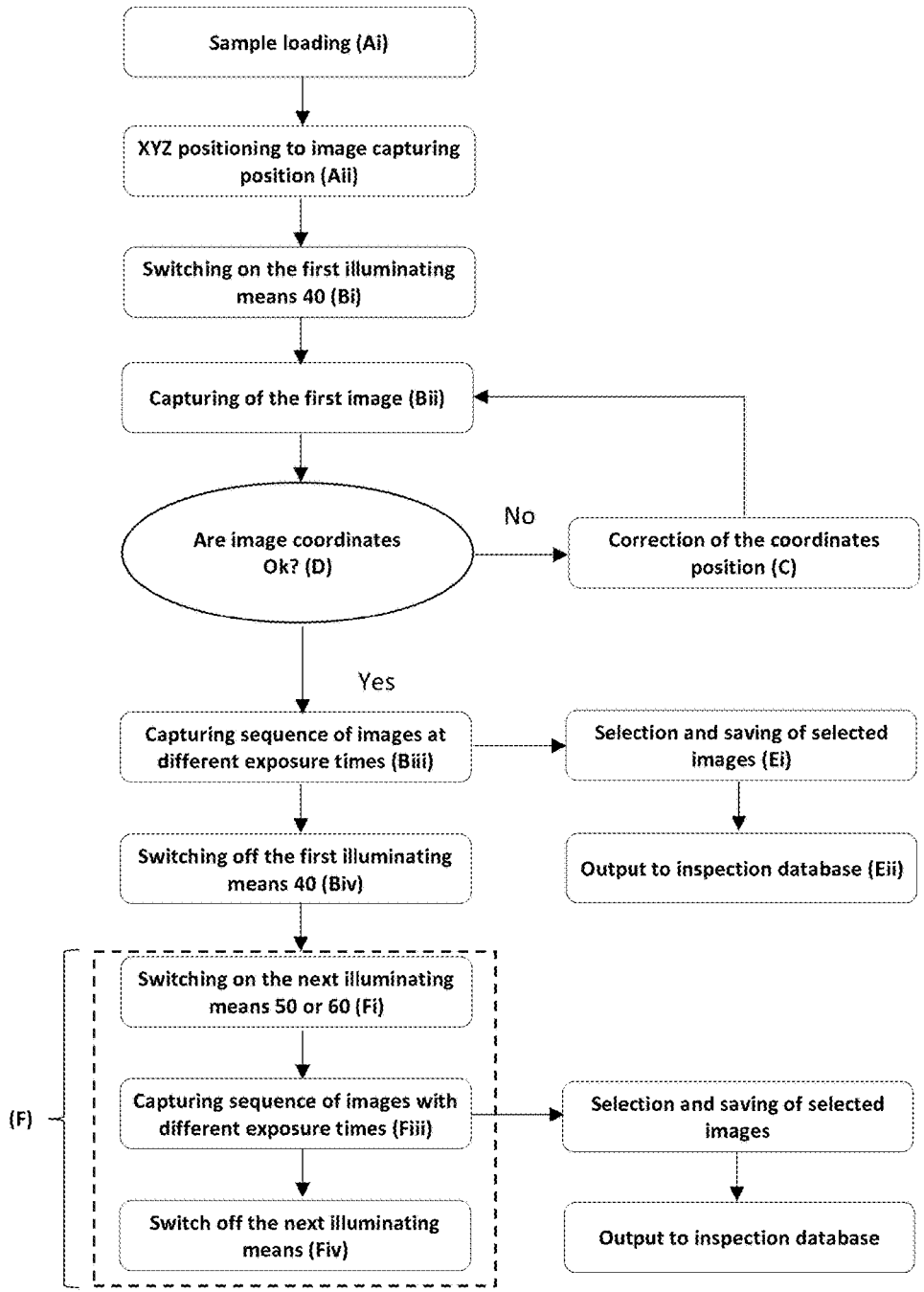
FIG. 10 is a flow diagram showing the steps in determining settings for use by an apparatus according to the present invention.

The determined suitable or preferred settings may then be applied in a high volume inspection process by the apparatus 10 being operated automatically under control of a processor to inspect a large number of optical components for a mass production. The steps of conducting the inspection can be similar to those as illustrated in FIG. 10, or may be varied according to different requirements and/or applications. The determined suitable or preferred settings can be applied to the high volume inspecting process so as to negate the need for further trial and error in terms of determining settings of the apparatus. The subsequent analysis of the captured images for defects can be conducted manually for a semi-automated process, but preferably automatically under the control of a computer processing apparatus or system for a fully automated inspection process.

Figure 11:
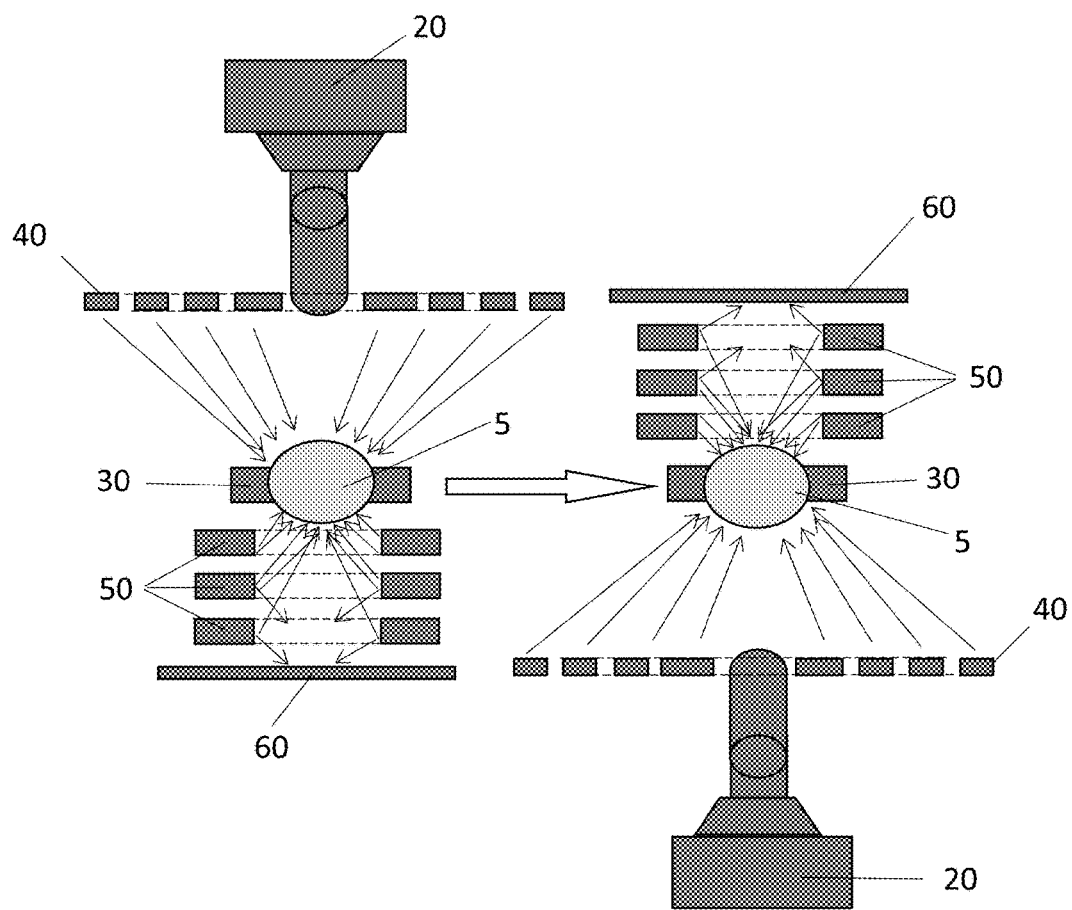
FIG. 11 is a schematic diagram showing a system for inspecting a light transmissive optical component according to the present invention.

In one further aspect, the present invention may further relate to a system for inspecting light transmissive optical components. The system may comprise two or more of the apparatuses 10 as described above, with the apparatuses 10 being arranged in a same orientation or different orientations relative to one another, as shown in FIG. 11, for example. The counter positioning of the two apparatuses in a system allows inspection to be conducted at both sides of the same optical lens, with both bright-field and dark-field inspections available at both sides of the lens to be inspected.

The present invention is advantageous in that it provides a method, an apparatus and a system for inspecting a light transmissive optical component such as an optical lens and that the apparatus is configurable to allow both bright-field and dark-field inspections of the optical component, with a wide range of exposures as well as adjustable illuminating angles being easily achievable. This is particularly advantageous in allowing different types of defects located at different regions or areas of the lens to be identified, detected and/or inspected at various brightnesses and contrasts. The apparatus is also highly adaptive to different types, forms, and configurations of optical components. More than one apparatus can be operated as a system with multiple checking stations, for example, and orientated in different or reversed directions to allow both sides of an optical lens to be inspected. The present invention also provides a method of conducting a semi or fully automated inspection of light transmissive optical components using the apparatus as described. The automated inspection enables optical components to be automatically inspected so as to allow an inspection of optical components at high volume. The present invention provides an efficient and systematic way to inspect quality of light transmissive optical components, negating the need for manual or visual inspection. The inspection is reliable, objective and bias-free. The analysis of the captured images may further be implemented through a computer interface to further enhance efficiency of the process.

The present description illustrates the principles of the present invention. It will thus be appreciated that those skilled in the art will be able to devise various arrangements that, although not explicitly described or shown herein, embody the principles of the invention and are included within its spirit and scope.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims hereof, any element expressed as a means for performing a specified function is intended to encompass any way of performing that function. The invention as defined by such claims resides in the fact that the functionalities provided by the various recited means are combined and brought together in the manner which the claims call for. It is thus regarded that any means that can provide those functionalities are equivalent to those shown herein.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art is referred to herein, such reference does not constitute an admission that it forms a part of the common general knowledge in the art.

The invention claimed is:

1. An apparatus for inspecting a light transmissive optical component, comprising:

an image capturing module arranged on a first side of a support configured to hold a light transmissive optical component whilst it is being inspected;

one or more first illuminating means arranged on the first side of the support and adapted to illuminate from a first side of a light transmissive optical component held by said support;

one or more second illuminating means arranged on a second side of the support and adapted to illuminate from a second side of the light transmissive optical component held by said support, the second side of the support opposing the first side of said support;

one or more third illuminating means arranged on the second side of the support and adapted to provide transmissive illumination at the second side of the light transmissive optical component held by the support, the third illuminating means comprises one or more of an illuminating surface and a light blocking surface selectively operable and are arranged to face and substantially align with the second illuminating means on the second side of the support;

wherein the one or more first illuminating means, the one or more second illuminating means, and the one or more third illuminating means are adapted to be selectively switched on to enable the image capturing module to capture one or more bright field images and dark field images of the light transmissive optical component held by the support.

2. The apparatus according to claim 1, wherein the first illuminating means comprises a plurality of first illuminating means, each of which is adapted to independently illuminate from the first side of the light transmissive optical component held by said support at different illuminating angles.

3. The apparatus according to claim 1, wherein the first illuminating means comprises an annular configuration.

4. The apparatus according to claim 3, wherein the first annular illuminating means comprises a plurality of first annular illuminating means arranged concentrically to one another.

5. The apparatus according to claim 1, wherein the second illuminating means comprises an annular configuration with a free space central passage substantially aligned with an axis passing through the first side and the second side of the support.

6. The apparatus according to claim 5, wherein the second illuminating means comprises a plurality of second illuminating means, each of which is adapted to independently illuminate from the second side of the light transmissive optical component held by said support at different illuminating angles.

7. The apparatus according to claim 6, wherein the plurality of second annular illuminating means are arranged coaxially to one another.

8. The apparatus according to claim 1, wherein the third illuminating means comprises a planar structure with the illuminating surface facing the second illuminating means on the second side of the support.

9. The apparatus according to claim 1, wherein the third illuminating means comprises an electronic display unit.

10. The apparatus according to claim 1, wherein the support is movable along at least one of an x-, y- and x-coordinate axis between the first illuminating means and the second illuminating means.

11. The apparatus according to claim 1, wherein the support is adapted to support a plurality of light transmissive optical components, the support is movable to align and position respective one of the plurality of light transmissive optical components between the at least one first illuminating means and the at least one second illuminating means.

12. A system for inspecting a light transmissive optical component comprising two or more apparatuses according to claim 1 arranged in a same or different orientations relative to one another.

13. A method of conducting an automated inspection of light transmissive optical components using the apparatus according to claim 1, comprising:
  positioning a light transmissive optical component at an image capturing position of the apparatus;
  actuating one or more of the first illuminating means and the second illuminating means of the apparatus;
  capturing a sequence of images of the light transmissive optical component under different configurations of the first illuminating means and the second illuminating means; and
  analyzing the sequence of images to identify a defect of the light transmissive optical component being inspected.

14. The method according to claim 13, wherein the actuating step comprises actuating one or more of the first illuminating means, the second illuminating means and a third illuminating means of the apparatus, the third illuminating means being arranged on the second side of the support and adapted to illuminate the second side of the light transmissive optical component held by the support, wherein the third illuminating means comprises at least one illuminating surface arranged to face and substantially align with the second illuminating means on the second side of the support.

15. The method according to claim 14, wherein the actuating step and the capturing step comprise:
  actuating one at a time the first illuminating means, the second illuminating means, and the third illuminating means in an arbitrary or a predetermined sequence; and after each actuation of a respective illuminating means, capturing a sequence of images of the light transmissive optical component under different configurations of the first illuminating means, the second illuminating means and the third illuminating means.

16. The method according to claim 14, wherein the actuating step and the capturing step comprise:
  simultaneously actuating a first combination of two illuminating means selected from the first illuminating means, the second illuminating means, and the third illuminating means; and after actuation of the first combination of illuminating means, capturing a sequence of images of the light transmissive optical component under different configurations of the first combination of illuminating means; and
  simultaneously actuating a second combination of two illuminating means selected from the first illuminating means, the second illuminating means, and the third illuminating means, with the second combination being different to the first combination; and after actuation of the second combination of the illuminating means, capturing a sequence of images of the light transmissive optical component under different configuration of the second combination of the illuminating means.

17. The method according to claim 13, wherein the first illuminating means comprises a plurality of first illuminating means, the method further comprises a step of adjusting illuminating angle from the first illuminating means by selectively actuating one or more of the plurality of first illuminating means prior to the image capturing step.

18. The method according to claim 13, wherein the second illuminating means comprises a plurality of second illuminating means, the method further comprises a step of adjusting illuminating angle from the second illuminating means by selectively actuating one or more of the plurality of second illuminating means prior to the image capturing step.

19. The method according to claim 13, wherein the sequence of images are taken under a changing shutter speed of the image capturing module.

20. The method according to claim 13, further comprising a step of outputting the captured sequence of images to a computer storage medium or database.

* * * * *